United States Patent [19]

Honeycutt

[11] Patent Number: 5,268,222

[45] Date of Patent: Dec. 7, 1993

[54] COMPOSITE FABRIC

[75] Inventor: Travis W. Honeycutt, Gainesville, Ga.

[73] Assignee: Isolyser Co., Inc., Norcross, Ga.

[21] Appl. No.: 9,824

[22] Filed: Jan. 26, 1993

Related U.S. Application Data

[63] Continuation-in-part of Ser. No. 881,685, May 12, 1992, Pat. No. 5,207,837, which is a continuation-in-part of Ser. No. 683,290, Apr. 10, 1991, abandoned.

[51] Int. Cl.$^5$ .................. A61B 19/08; A61F 13/15; A61F 13/46; B32B 33/00

[52] U.S. Cl. .................................. 428/224; 2/48; 2/49.4; 2/59; 2/171; 5/487; 5/490; 5/495; 112/440; 128/849; 128/DIG. 24; 134/42; 428/225; 428/229; 428/252; 428/253; 428/286; 428/340; 428/500; 428/913

[58] Field of Search .................. 2/48, 49 R, 59, 171; 112/440; 5/487, 490, 495; 156/281; 128/849, DIG. 24; 428/224, 225, 229, 252, 253, 286, 340, 500, 913; 602/41; 604/304, 364, 372; 134/42

[56] References Cited

U.S. PATENT DOCUMENTS

| | | |
|---|---|---|
| 3,089,493 | 5/1963 | Galindo ........................ 604/344 |
| 3,314,809 | 4/1967 | Klug . |
| 3,413,229 | 11/1968 | Bianco . |
| 3,484,874 | 12/1969 | Bickenheuser . |
| 3,859,125 | 1/1975 | Miller . |
| 3,886,610 | 6/1975 | Shelden . |
| 4,343,133 | 8/1982 | Daniels, et al. . |
| 4,568,341 | 2/1986 | Mitchell et al. ................ 604/368 |
| 5,207,837 | 5/1993 | Honeycutt ........................ 134/42 |

FOREIGN PATENT DOCUMENTS

| | | |
|---|---|---|
| 8902229A | 8/1992 | Brazil . |
| 50288 | 4/1982 | European Pat. Off. . |
| 107576 | 5/1984 | European Pat. Off. . |
| 272816 | 6/1988 | European Pat. Off. . |
| 3017246 | 11/1981 | Fed. Rep. of Germany . |
| 72041741 | 10/1972 | Japan . |
| 61159995 | 7/1986 | Japan . |
| WO91/17210 | 11/1991 | PCT Int'l Appl. . |
| 386161 | 1/1933 | United Kingdom . |
| 1187690 | 4/1970 | United Kingdom . |
| 1374199 | 11/1974 | United Kingdom . |
| 2211088 | 6/1989 | United Kingdom . |
| 2211196 | 6/1989 | United Kingdom . |
| 2248842 | 4/1992 | United Kingdom . |

*Primary Examiner*—James C. Cannon
*Attorney, Agent, or Firm*—Malcolm B. Wittenberg

[57] ABSTRACT

A composite fabric and its method of disposal after use. Garments, linens, drapes, towels and other useful articles are provided as the composite of a reusable first component and a woven, non-woven, knitted or otherwise formed fabric of thermoplastic polyvinyl alcohol polymer as a second component. The second component is water soluble in temperatures above approximately 140° F. After use, the composite is subjected to water of sufficient temperature to substantially dissolve the thermoplastic polyvinyl alcohol component but not the reusable first component.

22 Claims, No Drawings

COMPOSITE FABRIC

RELATED APPLICATIONS

The present application is a continuation-in-part of U.S. application Ser. No. 881,685 filed on May 12, 1992, and now U.S Pat. No. 5,207,837, which is in turn a continuation-in-part of U.S. application Ser. No. 683,290, filed on Apr. 10, 1991, and now abandoned.

TECHNICAL FIELD OF INVENTION

The present invention involves a composite fabric which has both reusable and disposable components. The disposable components are composed of non-woven, woven, knitted or otherwise formed fabric of thermoplastic polymer fiber which is water soluble in temperatures only above approximately 140° F.

BACKGROUND OF THE INVENTION

Hospital patient care generates considerable quantities of infectious medical waste in primary and acute care facilities. Such facilities obviously have a need to provide various garments and other textile products for use by physicians and attending professionals as well as for bedding, draperies, towels and similar items.

At one time, virtually all garments and other textiles used in the medical environment were reusable. Reusable textiles were primarily woven fabrics from yarns and the yarns were primarily composed of cotton and other natural fibers. However, approximately four decades ago, synthetics began to be employed which included polymers such as nylon and polyester fibers. These yarns were primarily spun from staple fibers and very little texturized synthetic filaments were in use.

Beginning approximately thirty years ago, disposable garments, covers, linens and drapes were introduced t the medical venue. These disposables offered many cost and time-saving features. For example, hospitals were able to reduce or entirely eliminate their laundry facilities and the hospital had, for the first time, garments that exhibited significant barrier protection.

One of the principal reasons why medical facilities were turning to disposables was that reusables suffer from one principal physical disability, namely, that they cannot readily provide liquid barrier properties, especially after the initial two or three laundry cycles. This is particularly troublesome in light of the fact that reusables are expected to perform for at least eighteen laundry cycles.

Modern day disposables are generally non-wovens which are carded stock chemically bonded into fabrics. These carded webs are treated with adhesives or bonding agents and then calendared to form "paper-light" materials. Carded webs have been somewhat replaced by thermobond materials which have a softer "hand" but which suffer from cross-directional strengths.

The most technologically advanced disposables are produced from air-entangled and hydroentangled fibers which produce excellent fabrics. Principal among these is the Sontera ™ hydroentangled fabric offered by DuPont. Non-wovens are principally composed of polypropylene fibers, with the notable exception being Sontera ™, which is a polyester staple with cellulose wood pulp. These hydroentangled webs display the most textile-like "hand" as well as a high degree of dimensional strength. As such, Sontera ™ and like fabrics have been accepted for present day state-of-the-art medical gowns and drapes.

There is now a trend throughout the health care industry of converting back from disposable items to reusable, cleanable ones. Originally, the trend was to employ disposables wherever possible to promote antiseptic techniques in patient care to decrease the potential for cross-infections between patients, staff and the general public. The recent federal and state government regulations such as the Medical Waste Tracking Act of 1988 and the OSHA Medical Facility rules have resulted in a substantial increase in medical waste that must be classified as "infectious."

When a patient is admitted to a hospital, the patient produces approximately 55 pounds of medical waste per day. Approximately 20% of this waste is infectious. The current stated objective of the American Hospital Association and the Centers for Disease Control is to treat medical waste as soon as it is generated. Both organizations recognize that medical waste is primarily an occupational hazard for health care workers and not an environmental safety problem. The best way to deal with infectious medical waste is to disinfect it at the point of generation and dispose of the treated medical waste with minimum handling and storage on premises.

The need for an effective way to dispose of medical waste has been highlighted by the amendment made by to 29 C.F.R. §1910.1030 which provides for the federal regulation under the Occupational Safety And Health Act, 29 U.S.C. 655, 657 to control bloodborne pathogens. Specifically, the Act calls for the establishment of an exposure control plan, the containment of specimens of blood or other potentially infectious materials and the general tightening of precautionary measures to minimize the spread of disease. A safe and effective way to dispose of hospital waste in the form of soiled garments and apparel would greatly facilitate compliance with the above-referenced Act.

As a result, consumption of medical disposable woven or non-woven products has been growing at a rate of approximately 10% a year. In 1988, sales totaled approximately 1.155 Billion Dollars. It is projected that by 1992, sales of medical disposable non-Woven products will reach 1.54 Billion Dollars. Disposable medical fabrics are generally currently composed of thermoplastic fibers such as polyethylene, polypropylene, polyesters, polyamides and acrylics. These fabrics can also include mixtures of thermoset fibers such as polyamides, polyarimids and cellulosics. They are typically 10–100 g/yd$^2$ in weight and can be woven, knitted or otherwise formed by methods well known to those in the textile arts while the non-wovens can be thermobonded, hydroentangled, wet laid or needle punched again by methods which are well known in the textile arts.

Although there is clearly a benefit in the use of disposables in the medical arts by avoiding the necessity for human contact with medical waste in the cleaning of comparable reusables, non-biodegradable disposables are posing a problem which is only now being recognized. Landfill sites are becoming increasingly burdened with disposables which do not biodegrade for hundreds of years, if ever. As landfill sites become fully exploited, new sites must be found which are rightfully opposed by residents located proximate to proposed site locations. In addition, incineration fails to be a viable alternative. Waste disposal incinerators are woefully inadequate. In fact, it is estimated that up to 25% of all incinerators currently in use will be forced to close over the next ten years.

As noted previously, disposables are now increasing in disfavor because of the acute disposal problem they create. Reusable garments generally range in weights from 30 to 300 g/yd$^2$, and most often they are in the 50 to 100 g/yd$^2$ range. The synthetic non-woven structures are, in non-garment environments, as low as 15 g/yd$^2$ but most often for garments, the weight ranges from 35 to 50 g/yd$^2$ with 100 g/yd$^2$ fabrics being utilized for heavy duty coveralls and lab coats.

Recognizing this acute disposal problem, applicant's parent application, namely U.S. application Ser. No. 881,685 filed on May 12, 1992 (U.S. Pat. No. 5,207,387) teaches the fabrication of garments, linens, drapes, towels and other useful articles from thermoplastic polymer fabric of polyvinyl alcohol fiber which is water soluble only in temperatures above 37° C., the human body temperature, and insoluble at temperatures below 37° C. It was contemplated that disposal of such products in a hot water bath such as a washing machine at or near the boiling point of water dedicated solely to solubilizing garments, linens, drapes, towels and other useful articles would also be an effective disinfecting media. As such, two objects were accomplished in practicing this invention, namely, that the polymer or sheets would be disinfected and would be solubilized for disposal through a municipal sewer system. Not only would this lessen the burden now being imposed upon current landfill sites, but liquid sewer disposal would prove a comparative low cost technique in ridding the user of such used garments.

It is an object of the present invention to provide useful articles which, as composites, display the beneficial attributes of both reusables and disposables. This and other objects would be more readily appreciated when considering the following disclosure and appended claims.

SUMMARY OF THE INVENTION

The present invention is directed toward a composite fabric as well as to a method of laundering the composite fabric after being subjected to potentially infectious waste material. The composite fabric comprises a first reusable component being substantially insoluble in aqueous solutions such that the first component is capable of being repeatedly laundered in hot surfactant-loaded aqueous solutions without substantial loss of component integrity.

The second component of the composite is a polymeric fabric of polyvinyl alcohol which is water soluble only at temperatures above 140° F. and insoluble at temperatures below 140° F. It is contemplated that when the composite fabric is subjected to hot aqueous media above the threshold temperature, the reusable component is merely laundered and disinfected in the aqueous bath while the second component is separated from the first, dissolved and disposed of with the aqueous media.

DETAILED DESCRIPTION OF THE INVENTION

As previously noted, there is little doubt that reusables are making new inroads into the health care marketplace despite their obvious drawbacks. Principally, reusables, particularly after several wash cycles, lack any significant barrier properties. As such, infectious material upon contacting reusables tend to be absorbed by them greatly enhancing potential contact of infection-bearing media with the health provider. The potential risks are well recognized and are certainly significant. Reusables also provide a poor barrier to the migratry path of pathogens from hospital staff workers to patients. Patients and particularly those post-operative ones with open wounds are susceptible to pathogens from doctors, nurses and other care providers and it is important to provide a barrier to such migration.

Reusables are making a comeback simply because of the concern over the shear volume of disposables entering the solid waste stream. Disposables such as PVC, nylon, polyester and other synthetic thermoplastic and thermoset films and fabrics simply do not biodegrade in any reasonable period of time. As such, there remains a need for economical barrier protection for use with these reusable fabrics.

It has been proposed that simple films of, for example, polyethylene and polypropylene manufactured in the shape of gown fronts, aprons, sleeves, head covers, shoe covers and like items be employed as barriers. These can be used with reusable garments but represent a significant labor and occupational exposure hazard when the reusables are returned to the commercial launderer or the hospital's own facility for laundering. These non-water soluble barrier materials have to be hand sorted and segregated from the reusables to enable the reusables to be reprocessed while the barrier garments are sent on to a suitable solid waste disposal facility.

As noted, the present invention consists of a composite fabric comprising a first reusable component being substantially insoluble in aqueous solutions such that the first component is capable of being repeatedly laundered in hot surfactant-loaded aqueous solutions without substantial loss of component integrity. A second component is employed comprising a thermoplastic polymer fabric of polyvinyl alcohol which is water soluble only at temperatures above 140° F. and insoluble at temperatures below 140° F.

The second component composed of polymer sheet material comprises polyvinyl alcohol with or without acetyl groups, cross-linked or uncross-linked. Ideally, the second component comprises a polyvinyl alcohol homopolymer that has been highly crystallized by post-drawing or by heat annealing. Ideal for use in the present invention would be a highly crystallized totally saponified polyvinyl acetate. Commercially, polyvinyl alcohol sold under the trademark Vinex 1003 TM by Air Products can be used herein. Useful fibers are typically 0.5 denier to 5.0 denier and are preferably from 1.0 to 2.0 denier, most preferably sized at 1.2 to 1.5 denier. A commercially available product for use in practicing the present invention is either Type T-B (VEE 1290) or Type T-5 (VPB 101) which are each available from Kuralon as its PVA fiber. This material is sold in 44 mm. lengths. The T-B product is sized at 1.2 denier while the T-5 product is sold in 38 mm staple lengths of 1.5 denier.

The fabric making up the second component can be constructed by any well-known technique for making woven, non-woven, knitted or otherwise formed fabric. Such non-woven techniques useful for making such polymer sheets includes spin bonding, melt blowing or wet laying, hydroentangling with cold water and/or thermally bonding with 30–70% of the surface melted to form, for example, a diamond pattern. When products, such as diapers, are configured of sheets of suitable thermoplastic material, the sheets are approximately 1 to 6 mils in thickness and more preferably 1 to 3 mils in thickness and most preferably approximately 1.5 mils in thickness. Suitable non-woven fabrics or sheets are approximately from 50 to 500 g/yd$^2$, more preferably from 20 to 100 g/yd$^2$ and most preferably from 30 to 70 g/yd$^2$. The polyvinyl alcohol thermoplastic film can also be configured from sheets that have been inflation extruded, cast extruded and thermo-formed.

The barrier fabric or second component can be "combined" with the first or reusable component in any of a number of ways. For example, the hot water soluble barrier fabric can be cast in sheets and thermobonded, stitched or even joined by adhesive to the reusable fabric. If an adhesive is employed, it should ideally be hot water soluble to facilitate the reusability of the first component. The barrier fabric can also be employed as an overgarment to the reusable fabric without any formal "joining" per se. For example, the barrier fabric can be configured into an apron to be worn over traditional cotton or composite clothing or as a shoe covering with an elastic mouth.

The composite fabric of the present invention can be configured into a wide variety of products. In fact, there is virtually no limit to useful articles that can be prepared pursuant to the present invention. As examples, the composite fabric of the present invention can be configured into such items as drapes, towels, covers, wraps, gowns, head covers, face masks, shoe coverings, dressings, underpads, diapers, sheets, pillow covers, napkins, aprons, sleeves, gown fronts and table covers. In other words, the list of useful articles is limited only to the desire to provide the article with a barrier layer which is water soluble used in conjunction with a reusable garment.

I claim:

1. A composite fabric comprising a first reusable component being substantially insoluble in aqueous solutions such that said first component is capable of being repeatedly laundered in hot surfactant-loaded aqueous solutions without substantial loss of component integrity joined to a second component comprising a thermoplastic polymer fabric of polyvinyl alcohol which is water soluble only at temperatures above 140° F. and insoluble at temperatures below 140° F.

2. The composite fabric of claim 1 wherein said second component comprises a polyvinyl alcohol homopolymer that has been highly crystallized by postdrawing or by heat annealing.

3. The composite fabric of claim 1 wherein said second component comprises a polyvinyl alcohol that is produced from crystallized substantially totally saponified polyvinyl acetate.

4. The composite fabric of claim 1 wherein said second component comprises a thermoplastic polymer fabric woven, non-woven or knitted of said polyvinyl alcohol.

5. The composite fabric of claim 1 wherein said composite is configured as a member selected from the group consisting of drapes, towels, covers, wraps, gowns, head covers, face masks, shoe coverings, dressings, tapes, underpads, diapers, sheets, pillow covers, napkins, aprons, sleeves, gown fronts and table covers.

6. The composite fabric of claim 1 wherein said second component comprises a polyvinyl alcohol fabric in the weight range of approximately 15 to 500 grams per square yard.

7. The composite fabric of claim 1 wherein said second component comprises a polyvinyl alcohol fabric in the weight range of approximately 20 to 100 grams per square yard.

8. The composite fabric of claim 1 wherein said second component comprises a polyvinyl alcohol fabric in the weight range of approximately 30 to 75 grams per square yard.

9. The composite fabric of claim 1 wherein said second component comprises a polyvinyl alcohol fabric configured from sheets that have been inflation extruded, cast extruded or thermo-formed.

10. The composite fabric of claim 1 wherein said second component is thermobonded to said first component.

11. The composite fabric of claim 1 wherein said second component is stitched to said first component.

12. The composite fabric of claim 1 wherein said second component is adhesively joined to said first component.

13. A method of laundering a composite fabric, said composite fabric comprising a first reusable component being substantially insoluble in aqueous solutions such that said first component is capable of being repeatedly laundered in hot surfactant-loaded aqueous solutions without substantial loss of component integrity joined to a second component comprising a thermoplastic polymer fabric of polyvinyl alcohol which is water soluble only at temperatures above 140° F. and insoluble at temperatures below 140° F., wherein said method comprises subjecting said composite fabric to an aqueous media at a temperature above approximately 140° F. to launder said first reusable component and dissolve said second component wherein said second component is separated from said first reusable component and disposed of with said aqueous media.

14. The method of claim 13 wherein said first reusable component is joined With a new second component after said composite fabric has been laundered.

15. The method of claim 13 wherein said second component comprises a polyvinyl alcohol homopolymer that has been highly crystallized by postdrawing or by heat annealing.

16. The method of claim 13 wherein said second component comprises a polyvinyl alcohol that is produced from crystallized substantially totally saponified polyvinyl acetate.

17. A method of claim 13 wherein said second component comprises a thermoplastic polymer fabric woven, non-woven or knitted of said polyvinyl alcohol.

18. The method of claim 13 wherein said composite is configured as a member selected from the group consisting of drapes, towels, covers, wraps, gowns, head covers, face masks, shoe coverings, dressings, tapes, underpads, diapers, sheets, pillow covers, napkins, aprons, sleeves, gown fronts and table covers.

19. The method of claim 13 wherein said second component comprises a polyvinyl alcohol fabric in the weight range of approximately 15 to 500 grams per square yard.

20. The method of claim 13 wherein said second component comprises a polyvinyl alcohol fabric in the weight range of approximately 20 to 100 grams per square yard.

21. The method of claim 13 wherein said second component comprises a polyvinyl alcohol fabric in the weight range of approximately 30 to 75 grams per square yard.

22. The method of claim 13 wherein said second component comprises a polyvinyl alcohol fabric configured from sheets that have been inflation extruded, cast extruded or thermo-formed.

* * * * *